(12) United States Patent
Shih et al.

(10) Patent No.: US 8,708,557 B2
(45) Date of Patent: Apr. 29, 2014

(54) APPARATUS FOR MEASURING THERMAL DIFFUSIVITY

(75) Inventors: Chih-Chao Shih, Hsinchu (TW); Jin-Bao Wu, Hsinchu (TW); Ming-Sheng Leu, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 62 days.

(21) Appl. No.: 13/524,824

(22) Filed: Jun. 15, 2012

(65) Prior Publication Data

US 2013/0266038 A1 Oct. 10, 2013

(30) Foreign Application Priority Data

Apr. 9, 2012 (TW) .............................. 101112459 A (51) Int. Cl.
*G01N 25/20* (2006.01)
(52) U.S. Cl.
USPC .............................. 374/43; 374/120; 374/161
(58) Field of Classification Search
USPC .......................................... 374/43, 120, 161
See application file for complete search history.

(56) References Cited

U.S. PATENT DOCUMENTS

| | | | |
|---|---|---|---|
| 6,878,899 B2* | 4/2005 | Smart ...................... | 219/121.61 |
| 7,246,939 B1 | 7/2007 | Gultekin | |
| 8,212,213 B2* | 7/2012 | Myrick et al. ............. | 250/336.1 |
| 2006/0153269 A1 | 7/2006 | Lakestani et al. | |
| 2009/0324892 A1* | 12/2009 | Hasegawa et al. ............ | 428/172 |
| 2011/0113516 A1 | 5/2011 | Fink et al. | |

OTHER PUBLICATIONS

Philip G. Kosky, "A method of measurement of thermal conductivity: Application to free-standing diamond sheet", Rev. Sci. Instrum., vol. 64, No. 4, Apr. 1993, p. 1071-1075.
D. M. Bhusari, et al., "Traveling wave method for measurement of thermal conductivity of thin films", Rev. Sci. Instrum., vol. 68, No. 11, Nov. 1997, p. 4180-4183.

* cited by examiner

*Primary Examiner* — Mirellys Jagan
(74) *Attorney, Agent, or Firm* — J.C. Patents (57) ABSTRACT

An apparatus for measuring thermal diffusivity includes a Raman spectroscope, a heating device, and a signal analyzing unit. The Raman spectroscope is utilized to measure a Raman scattering intensity of different sites of a film to be measured. The heating device is utilized to provide a controllable thermal driving wave. The signal analyzing unit is utilized to analyze the Raman scattering intensity from the Raman spectroscope and the thermal driving wave so as to evaluate the thermal diffusivity of the film to be measured.

10 Claims, 6 Drawing Sheets

APPARATUS FOR MEASURING THERMAL DIFFUSIVITY

CROSS-REFERENCE TO RELATED APPLICATION

This application claims the priority benefit of Taiwan application serial no. 101112459, filed on Apr. 9, 2012. The entirety of the above-mentioned patent application is hereby incorporated by reference herein and made a part of this specification.

TECHNICAL FIELD

The technical field relates to an apparatus and a method for measuring thermal diffusivity.

BACKGROUND

In order to analyze the thermal diffusivity properties of a material, the thermal diffusivity can be calculated by applying one side of the material with heat and measuring the temperature at the other side. However, when the dimensions of the material is as small as on the nano scale, the direct measurement methods in the past are no longer suitable.

Currently, the methods for measuring thermal diffusivity include the flash method, the $3\omega$ method, the AC calorimetric method, the modulated laser technique, the instantaneous phase portrait method, and the traveling wave method. Although these measurement methods are mainly used to measure thermal diffusivity of nano scale films, many problems exist herein. For example, it is very difficult to measure the actual temperature of nano scale samples.

In order to avoid the foregoing difficulty, the thermal traveling wave method of measuring the thermal diffusivity of films was issued.

The thermal traveling wave method has been developed into many different forms, and the formula represented by equation (1) is the most representative:

$$\Delta\theta = 45 + \frac{180}{\pi}\sqrt{\frac{f\pi}{\alpha}}\,d \qquad (1)$$

In the equation (1), $\Delta\theta$ represents the phase difference between the thermal source and the thermal traveling wave at a distance d, f represents the frequency of the thermal traveling wave or the thermal source wave, and a represents the thermal diffusivity.

Since the aforementioned thermal traveling wave method employs an optical technique to perform the measurement, the signal is very weak and the diffraction limit issue has to be considered. Furthermore, the demands on the measurement environment are extremely strict, as any slight ambient vibration affects the signal of the thermal traveling wave. Moreover, the demands on the measure sample are also strict since the film to be measured must be mirror processed in order to reflect light. Due to the optical diffraction limit, the spatial resolution cannot be less than 250 nm, and the surface layer can be measured because multiple film measurement is not possible.

SUMMARY

One of exemplary embodiments comprises an apparatus for measuring thermal diffusivity. The apparatus at least includes a Raman spectroscope, a heating device, and a signal analyzing unit. The Raman spectroscope is used to measure a Raman scattering intensity of different sites of a film to be measured. The heating device is used to provide a controllable thermal driving wave for the film to be measured. The signal analyzing unit is used to analyze the Raman scattering intensity from the Raman spectroscope and the thermal driving wave, so as to obtain a thermal diffusivity of the film to be measured.

Another of exemplary embodiments comprises a method for measuring thermal diffusivity. The method includes using a thermal source to provide a controllable thermal driving wave for a film to be measured, and then detecting the variation waves of the Raman scattering intensity at a plurality of sites of the film to be measured. The thermal driving wave and the intensity variation waves of the sites are then compared to obtain a plurality of phase differences, and a thermal diffusivity of the film to be measured is calculated according to the phase differences.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DESCRIPTION OF EMBODIMENTS

The following are detailed descriptions of the disclosure in association with the accompanied figures.

Figure 1:
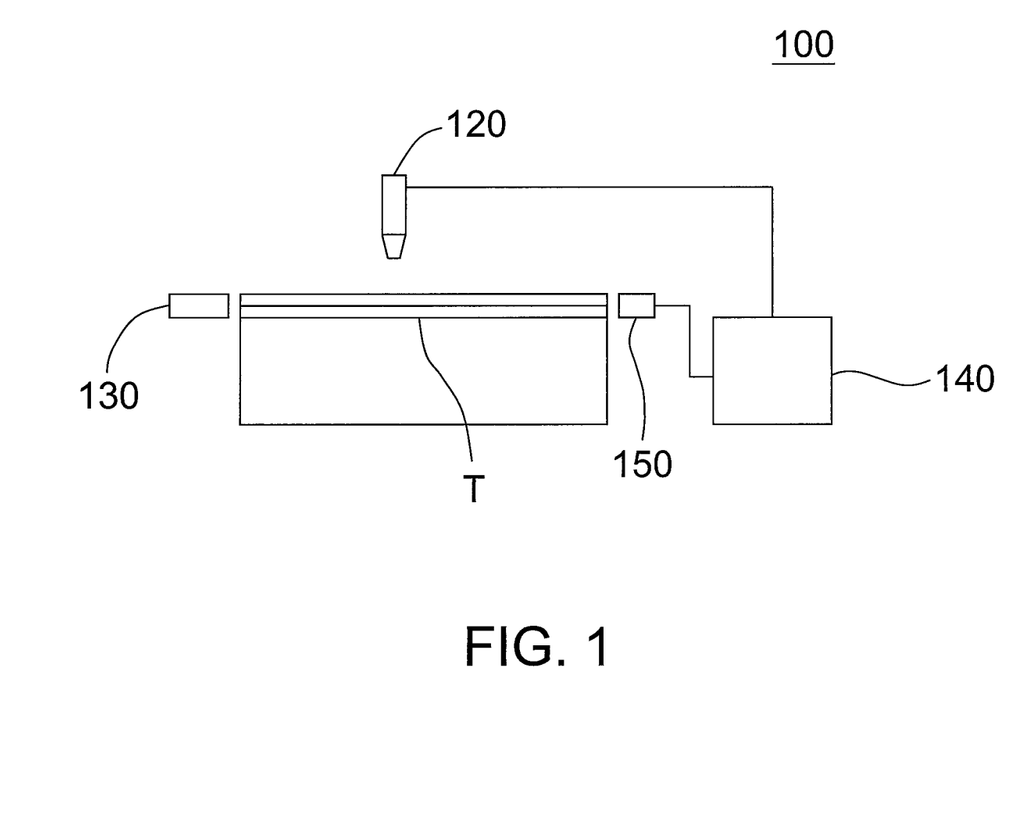
FIG. 1 is a schematic view of an apparatus for measuring thermal diffusivity according to an exemplary embodiment.

FIG. 1 is a schematic view of an apparatus for measuring thermal diffusivity according to an exemplary embodiment.

With reference to FIG. 1, an apparatus for measuring thermal diffusivity 100 of the exemplary embodiment includes a Raman spectroscope 120, a heating device 130, and a signal analyzing unit 140.

The Raman spectroscope 120 is utilized to measure a Raman scattering intensity of different sites of a film to be measured T. The Raman spectroscope 120 may be a LabRAM HR Raman Microscope from Horiba Co., although embodiments of the disclosure are not limited thereto. The type of Raman spectroscope 120 in the present embodiment is not limited, as long as the Raman spectroscope is one which can measure the Raman scattering intensity of different sites of the film to be measured T. The Raman spectroscope 120 used in the present embodiment may be a commercially available Raman spectroscope. The light source used in the Raman spectroscope 120 is selected according to factors such as the material and thickness of the film to be measured T. For example, when the film to be measured T is a single layer film, and the thermal diffusivity of the surface layer of the single layer film is to be measured, then the transmission depth of the light source for the Raman spectroscope needs to reach the surface layer. That is, as long as the Raman spectrum of the surface layer of the single layer film can be measured. Alternatively, when the thermal diffusivities of all layers of a multi-layer film are to be measured, the transmission depth of the light source for the Raman spectroscope needs to reach the bottommost layer of the multi-layer film. In other words, the transmission depth of the light source needs to be sufficient so the Raman spectrum of the bottommost layer of the multi-layer film can be measured.

The heating device 130 is utilized to provide a controllable thermal driving wave for the film to be measured T. In order to provide the thermal driving wave for the film to be measured T, the heating device 130 may be a heating unit with a controllable heating frequency and a power. The heating unit with the controllable heating frequency and power includes a laser heating unit, a resistive heating unit, or a mechanical wave heating unit. A range of laser used in the laser heating unit ranges from visible light (between 400-700 nm), near infrared (IR) light (between 700-2000 nm), or near ultraviolet (UV) light (300-400 nm). The heating device 130 of the present embodiment is not limited, and is suitably selected according to the material of the film to be measured T. When the material of the film to be measured T is an insulating material, the heating device 130 is preferably a resistive heating unit providing heat through a heating wire coated on the film to be measured T.

Except for the heating device 130, the apparatus for measuring thermal diffusivity 100 may further include a detecting unit 150. The detecting unit 150 is utilized to detect the thermal driving wave provided by the heating device 130, and transmitting the detected thermal driving wave to the signal analyzing unit 140.

The signal analyzing unit 140 is utilized to analyze the Raman scattering intensity from the Raman spectroscope 120 and the thermal driving wave, so as to obtain a thermal diffusivity of the film to be measured T. Specifically, the signal analyzing unit 140 contains the signals of the Raman scattering intensity of different sites of the film to be measured from the Raman spectroscope 120 and the thermal driving wave from the heating device 130. The Raman spectrum at the same location on the film to be measured T is affected by the thermal driving wave, such that the temperature of the film to be measured T changes, and the Raman scattering intensity in the Raman spectrum varies with time. Accordingly, the intensity variation wave at this site can be sampled. Therefore, within the same time period, a phase difference AO can be obtained by comparing the thermal driving wave with the intensity variation wave. When the measurement site is changed and the above measurement and comparison are repeated, because the intensity variation wave travels past a different location, the phase compared to the thermal driving wave is also different. Accordingly, another phase difference $\Delta\theta$ can be obtained.

The thermal diffusivity of the film to be measured T can be derived by using the aforementioned thermal traveling wave method and bringing the phase difference $\Delta\theta$ into the equation (1) for calculating the thermal diffusivity. However, embodiments of the disclosure are not limited thereto, and any thermal traveling wave methods using the phase difference $\Delta\theta$ to derive the thermal diffusivity can be used.

Compared to conventional thermal diffusivity measurement apparatuses, the apparatus for measuring thermal diffusivity according to an exemplary embodiment has at least the following properties: strict control of the measurement environment is not needed; the resolution can reach the nano scale, which means that the thermal diffusivity of the film to be measured T can be measured even if the thickness is on the nano scale; the thermal diffusivity of each layer in a multi-layer film can be simultaneously obtained; and the demands on the film to be measured T is low, which means the film to be measured T does not need to be processed before measurement.

Figure 2:
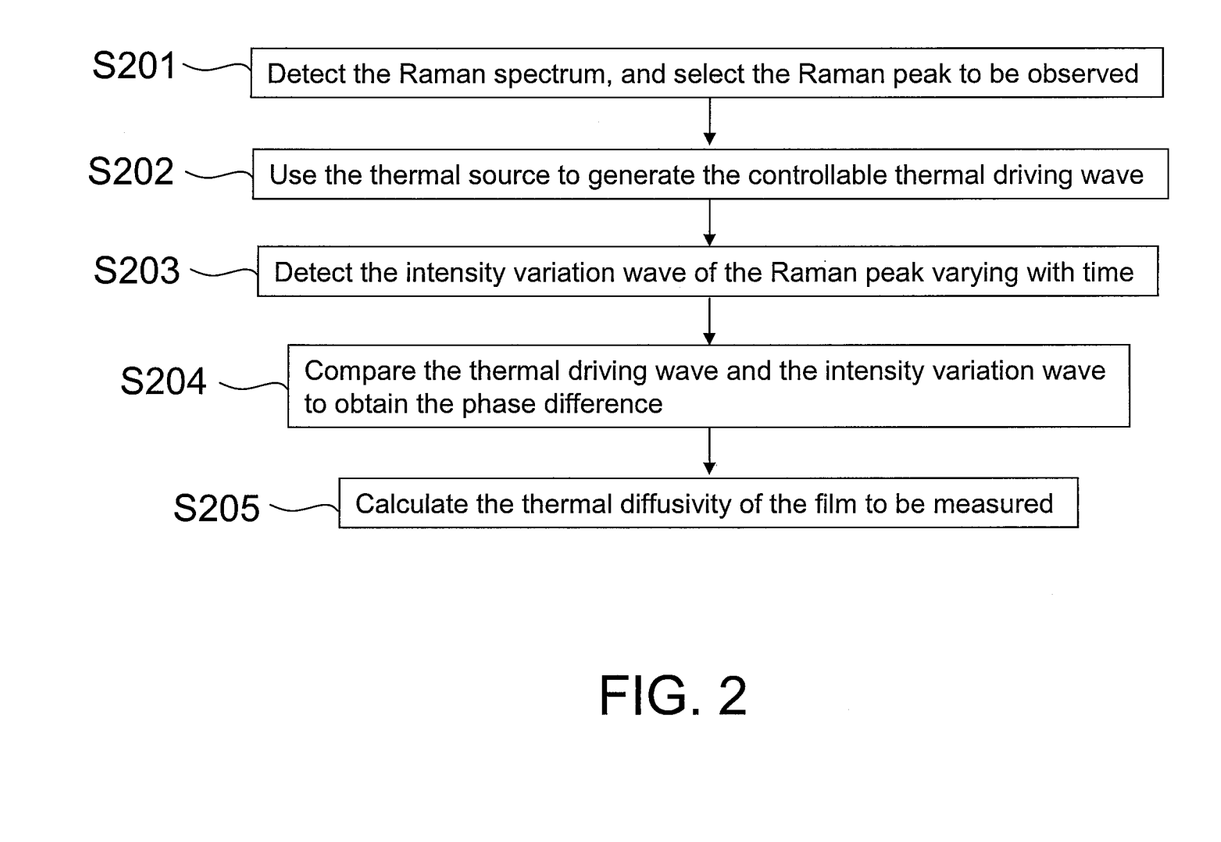
FIG. 2 is a flow diagram of a method for measuring thermal diffusivity according to an exemplary embodiment.

FIG. 2 is a flow diagram of a method for measuring thermal diffusivity according to an exemplary embodiment.

With reference to FIG. 2, the method for measuring thermal diffusivity may be performed on the apparatus for measuring thermal diffusivity 100 in the previous embodiment, although embodiments of the disclosure are not limited thereto. The apparatus in FIG. 1 is merely used for illustrative purposes so that a person having ordinary skill in the art can fully understand the measurement method in the present embodiment. The measurement method includes the following steps.

In Step S201, a Raman spectrum is measured and a Raman peak to observe is selected.

The Raman spectroscope 120 is utilized to scan the Raman spectrum of the film to be measured T. The Raman spectrum scanned in Step S201 is the Raman spectrum of the entire film to be measured T. When the film to be measured T is a single layer film, since the peak of the measured Raman spectrum corresponds to the material of the single layer film, this peak is chosen as the Raman peak to be observed in the subsequent steps. When the film to be measured T is a multi-layer film, the measured Raman spectrum has a plurality of peaks, and each peak respectively corresponds to the material of each layer in the multi-layer film. The peak selected here represents the Raman peak to be observed in the subsequent steps. In addition, if the thermal diffusivity of the surface layer of the multi-layer film is to be measured, then the light source of the Raman spectroscope 120 is adjusted such that the transmission depth thereof reaches the surface layer of the multi-layer film. Accordingly, the measured peak can serve as the Raman peak to be observed in the subsequent steps. However, embodiments of the disclosure are not limited thereto. In alternative embodiment, Step S201 may be omitted and the method directly enters into Step S202, and the Raman peak to be observed is selected in Step S203.

In Step S202, a thermal source is utilized to generate a controllable thermal driving wave.

The heating device 130 is then utilized to generate a controllable thermal driving wave on the sample. To be specific, the thermal driving wave may be generated by a heating unit with a controllable heating frequency and power, such that a controllable thermal traveling wave can be driven on the film to be measured T. Moreover, the detecting unit 150 may be utilized to transmit the signals from the heating device 130 to the signal analyzing unit 140. In one embodiment, a near IR heating unit provides a thermal driving wave from one end of the film to be measured T.

In Step S203, an intensity variation wave of the Raman scattering varying with time is detected.

The Raman spectroscope 120 is then utilized to measure the Raman scattering intensity variation wave of an original site of the film to be measured T. Due to the thermal driving wave, the temperature at the original site of the film to be measured T changes. Therefore, the Raman scattering intensity measured at the original site of the film to be measured T varies, and accordingly the intensity variation wave is generated. That is, the intensity variation wave varying with time is the thermal traveling wave generated by detecting the Raman effect on the original site of the film to be measured T.

In Step S204, the intensity variation wave and the thermal driving wave are compared to obtain a phase difference.

The thermal driving wave obtained in Step S202 is compared with the intensity variation wave obtained in Step S203 in order to obtain the phase difference of the thermal traveling wave passing through the original site. The measurement site is then changed, and Steps S202-S204 are repeated to obtain a phase difference of another site. The intensity variation wave has different phase differences corresponding to the wave passing through different sites, and a quantity of the sites measured is at least three sites, for example.

In Step S205, a thermal diffusivity of the film to be measured is calculated.

The thermal diffusivity of the film to be measured T can then be derived by using a thermal traveling wave method and bringing the plurality of phase differences obtained in Step S204 into above equation (1) for calculating the thermal diffusivity. However, embodiments of the disclosure are not limited thereto, and any thermal traveling wave methods using the phase differences to derive the thermal diffusivity can be used.

Accordingly, the method for measuring thermal diffusivity according to above exemplary embodiment does not require strict control of the measurement environment to measure the thermal diffusivity of each layer in a multi-layer film having thickness down to the nano scale. Moreover, little demands are placed on the film to be measured, and the method is suitable for various types of films.

Furthermore, after measuring films of different materials by the method for measuring thermal diffusivity according to above exemplary embodiment, a database can be established based on measured data corresponding to each material such as the intensity variation values of the Raman peaks, the phase differences, and the thermal diffusivities, for example. The temperature of the film to be measured may be deduced according to this database.

The following experiments further specify the embodiments of the disclosure.

Experiment 1

Sample to be measured (Film/Substrate): diamond like carbon (DLC) 180 nm/Si (100) substrate.

Raman spectroscope: LabRAM HR Raman Microscope from Horiba Co., HeNe Laser: 632.8 nm wavelength, power: 20 mW; zoom rate: object lens 100×, aperture 0.9; image resolution: calibrated focal length 1 µm.

Heating device: near IR heating unit, temperature control range 50° C.-82° C.

The sample to be measured is loaded on a platform, and the Raman spectroscope is utilized to measure the Raman spectrum of the sample to be measured. A peak located at a Raman shift of 519.12 $cm^{-1}$ and another peak located at a Raman shift of approximately 1550 $cm^{-1}$ are obtained. The peak at the Raman shift of 519.12 $cm^{-1}$ is a signal representing silicon (Si), and the peak at the Raman shift of 1550 $cm^{-1}$ is a signal representing DLC.

Figure 3:
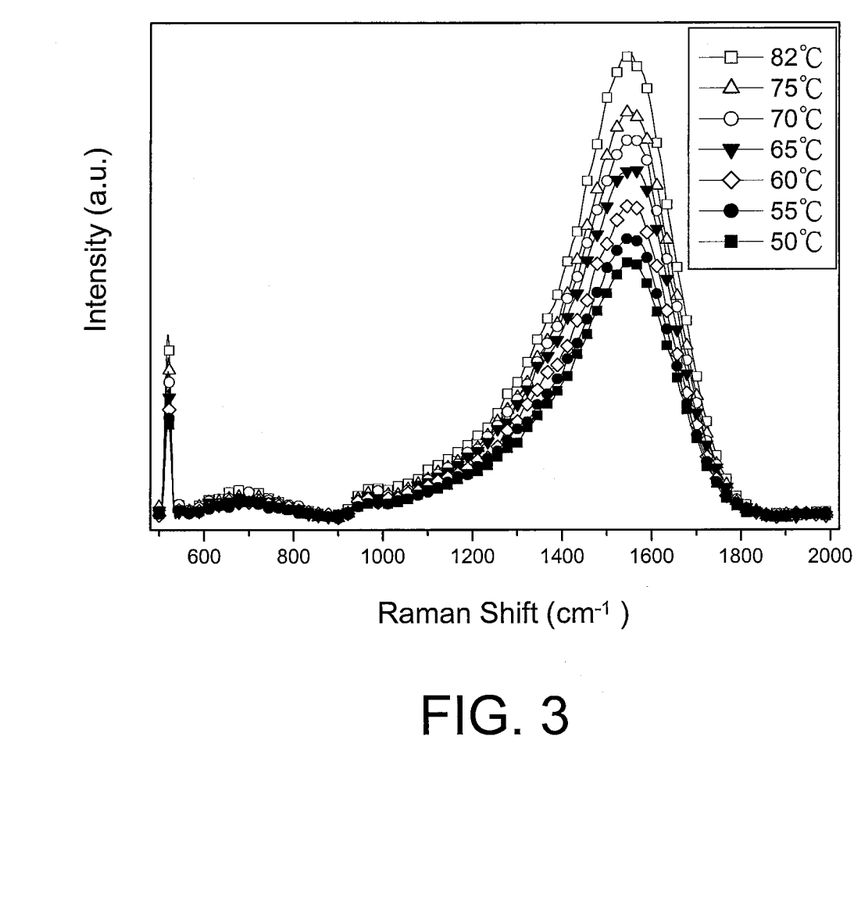
FIG. 3 is a curve diagram of the peak intensity variations for the Raman peaks under influence by the thermal driving wave in Experiment 1.

The near IR heating unit is then utilized to provide a thermal driving wave from one end of the sample to be measured. Any site on the sample is then selected to measure the Raman spectrum. FIG. 3 is a curve diagram of the peak intensity variations for the Raman peaks under influence by the thermal driving wave in Experiment 1. As shown in FIG. 3, when influenced by the thermal driving wave, the temperature of the sample to be measured changes, and the peak intensities of the Raman peaks also vary significantly.

Figure 4:
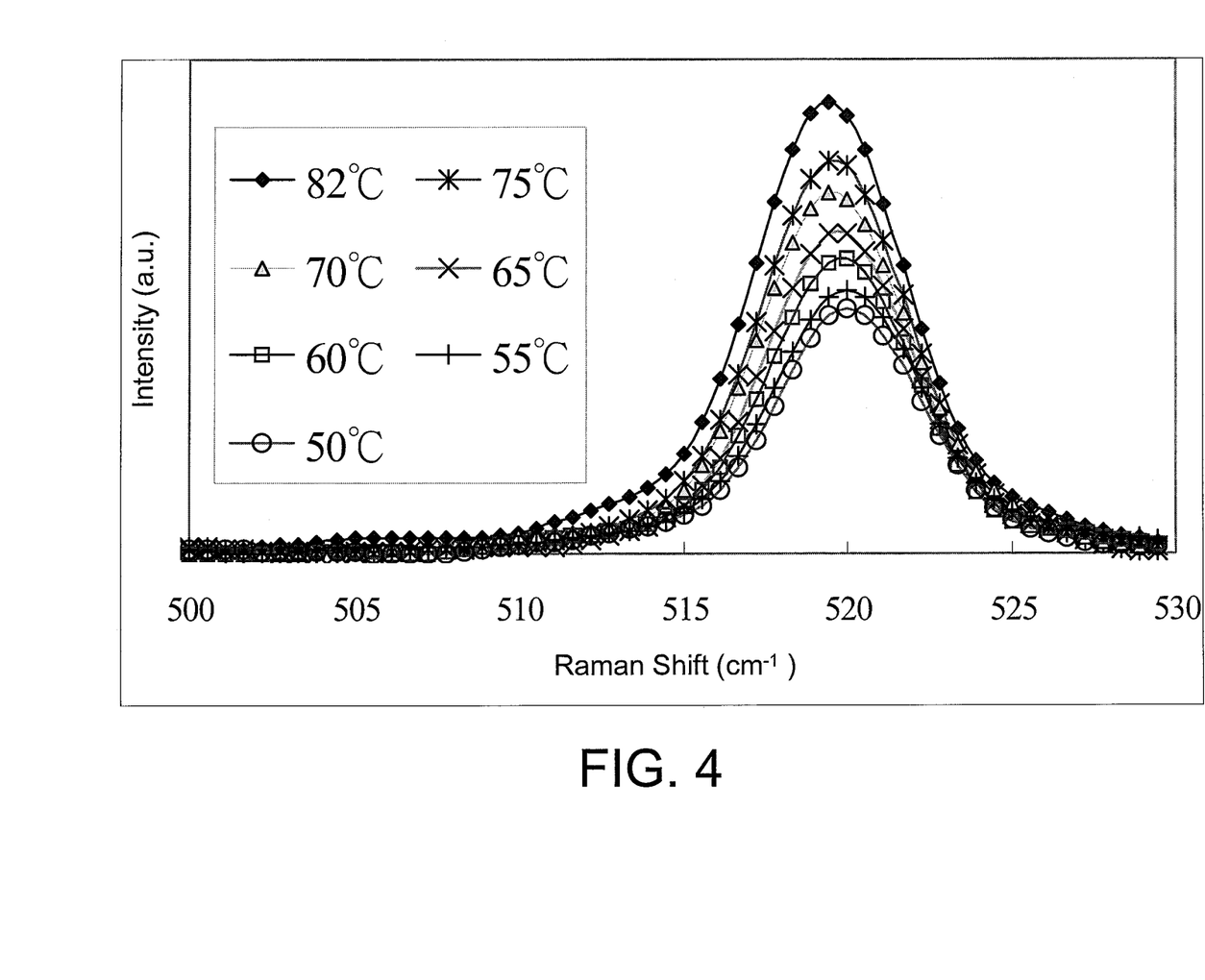
FIG. 4 is a magnified curve diagram of the location of the signal peak representing silicon (Si) in FIG. 3.
Figure 5:
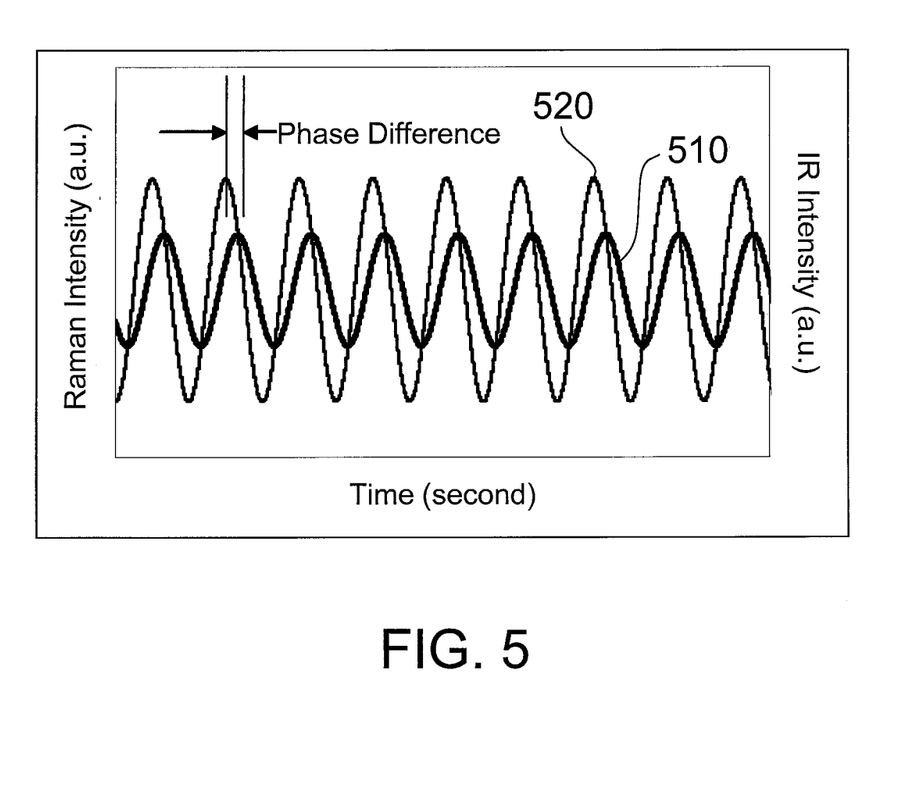
FIG. 5 is a curve diagram of a peak intensity variation wave 510 for the Raman peaks of the signal representing Si and a thermal driving wave 520.
Figure 6:
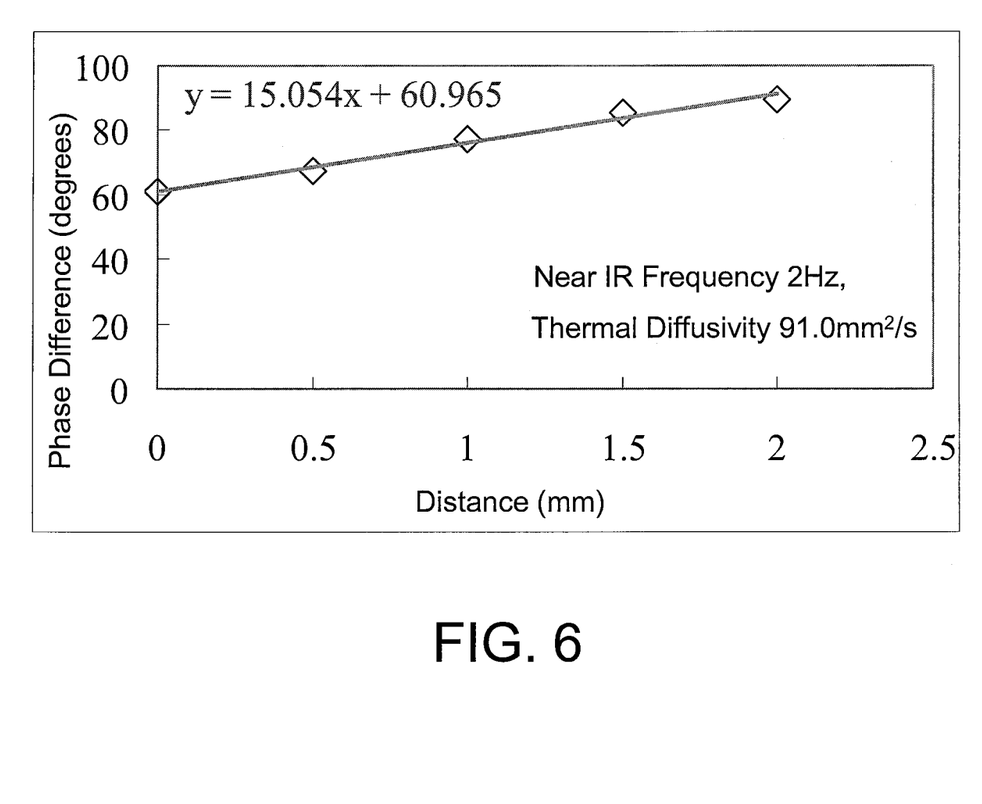
FIG. 6 is a relational diagram of the phase differences and the distances in Experiment 1.

The peak of the signal representing Si is selected as the Raman peak to be observed. FIG. 4 is a magnified curve diagram for the location of the signal peaks representing Si in FIG. 3. FIG. 5 is a curve diagram of a peak intensity variation wave 510 for the Raman peaks of the signal representing Si and a thermal driving wave 520. By graphing the peak intensities of the signal peaks representing Si in FIG. 4 versus time, the peak intensity variation wave 510 depicted in FIG. 5 can be obtained. In order to compare the phase difference between the thermal driving wave 520 and the peak intensity variation wave 510, the thermal driving wave is also shown in FIG. 5 so as to compare the phase difference of the two waves. Another site on the sample to be measured is then selected, and the aforementioned steps are repeated to obtain a plurality of phase differences. The other sites referred to herein are different locations relative to the thermal source (near IR heating unit). FIG. 6 is a relational diagram of the phase differences and the distances in Experiment 1. The distance referred to herein is a distance the thermal traveling wave travels to the measurement site. By graphing the obtained phase differences and distances, a straight line shown in FIG. 6 can be obtained. According to the thermal traveling wave method shown in foregoing equation (1) for example, the thermal diffusivity of the Si substrate can be calculated using the slope in FIG. 6, and the result from the measurement calculation is about 91.0 $mm^2/s$.

As above, Steps S202-S205 are repeated after the signal peak representing DLC is selected as the Raman peak to be observed, and accordingly the thermal diffusivity of the DLC can be obtained.

In view of the foregoing, the apparatus and method for measuring thermal diffusivity according to an exemplary embodiment do not require strict control of the measurement environment to measure the thermal diffusivity of each layer in a multi-layer film having thickness down to the nano scale. Moreover, little demands are placed on the film to be measured, and the apparatus and method are suitable for various types of films.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An apparatus for measuring thermal diffusivity, comprising:
    a Raman spectroscope, measuring a Raman scattering intensity of different sites of a film to be measured;
    a heating device, providing a controllable thermal driving wave for the film to be measured; and
    a signal analyzing unit, analyzing the Raman scattering intensity from the Raman spectroscope and the thermal driving wave, so as to obtain a thermal diffusivity of the film to be measured.

2. The apparatus for measuring thermal diffusivity as claimed in claim 1, wherein the thermal diffusivity of the film to be measured is obtained from a phase difference variation of the Raman scattering intensities and the thermal driving wave.

3. The apparatus for measuring thermal diffusivity as claimed in claim 1, further comprising a detecting unit used to detect the thermal driving wave provided by the heating device and to transmit a detected signal of the thermal driving wave to the signal analyzing unit.

4. The apparatus for measuring thermal diffusivity as claimed in claim 1, wherein the film to be measured is a single layer film.

5. The apparatus for measuring thermal diffusivity as claimed in claim 1, wherein the film to be measured is a multi-layer film.

6. The apparatus for measuring thermal diffusivity as claimed in claim 1, wherein when the film to be measured is a single layer film, the Raman spectroscope measures a Raman signal of a surface layer of the single layer film.

7. The apparatus for measuring thermal diffusivity as claimed in claim 1, wherein when the film to be measured is a multi-layer film, the Raman spectroscope measures a Raman signal of the films below a surface layer of the multi-layer film.

8. The apparatus for measuring thermal diffusivity as claimed in claim 1, wherein the heating device is a heating unit with a controllable heating frequency and a power.

9. The apparatus for measuring thermal diffusivity as claimed in claim 8, wherein the heating unit with the controllable heating frequency and the power comprises a laser heating unit, a resistive heating unit, or a mechanical wave heating unit.

10. The apparatus for measuring thermal diffusivity as claimed in claim 9, wherein a range of a laser used in the laser heating unit ranges from visible light, near infrared light, or near ultraviolet light.

\* \* \* \* \*